(12) United States Patent
Arcot-Krishnamurthy et al.

(10) Patent No.: US 9,393,415 B2
(45) Date of Patent: Jul. 19, 2016

(54) SYSTEMS AND METHODS FOR USING ELECTRICAL IMPEDANCE FOR NEURO CARDIAC THERAPY

(75) Inventors: Shantha Arcot-Krishnamurthy, Vadnais Heights, MN (US); Yi Zhang, Plymouth, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 388 days.

(21) Appl. No.: 13/309,320

(22) Filed: Dec. 1, 2011

(65) Prior Publication Data

US 2012/0172742 A1  Jul. 5, 2012

Related U.S. Application Data

(60) Provisional application No. 61/427,978, filed on Dec. 29, 2010.

(51) Int. Cl.
| | | |
|---|---|---|
| *A61B 5/02* | (2006.01) | |
| *A61N 1/36* | (2006.01) | |
| *A61B 5/053* | (2006.01) | |
| *A61N 1/365* | (2006.01) | |

(52) U.S. Cl.
CPC .......... *A61N 1/36053* (2013.01); *A61B 5/0538* (2013.01); *A61N 1/36117* (2013.01); *A61N 1/36135* (2013.01); *A61N 1/36521* (2013.01)

(58) Field of Classification Search
CPC .................................................... A61B 5/0809
USPC ......................................................... 600/536
See application file for complete search history.

(56) References Cited

U.S. PATENT DOCUMENTS

| | | | |
|---|---|---|---|
| 8,433,419 B2 | 4/2013 | Chavan et al. | |
| 8,483,831 B1 | 7/2013 | Hlavka et al. | |
| 8,594,805 B2 | 11/2013 | Hincapie Ordonez et al. | |
| 2005/0107843 A1* | 5/2005 | McDermott et al. | ............ 607/57 |

(Continued)

FOREIGN PATENT DOCUMENTS

| | | |
|---|---|---|
| JP | 2010519960 A | 6/2010 |
| JP | 2014509879 A | 4/2014 |

OTHER PUBLICATIONS http://fclass.vaniercollege.qc.ca/~vickerdt/course_materials/Physiology%20of%20the%20voice.pdf.*

(Continued)

*Primary Examiner* — Patricia Mallari
*Assistant Examiner* — Vasuda Ramachandran
(74) *Attorney, Agent, or Firm* — Schwegman Lundberg & Woessner, P.A.

(57) ABSTRACT

A device embodiment is configured to deliver vagal stimulation therapy (VST) to a vagus nerve of a patient. The device embodiment includes a neural stimulator, an implantable impedance sensor and an impedance analyzer. The neural stimulator is configured to deliver the VST to the vagus nerve in a cervical region of the patient. The implantable impedance sensor is configured to detect impedance changes in a cervical region of the patient caused by laryngeal vibrations. The impedance sensor is configured to generate sensed impedance values. The impedance analyzer is configured to analyze the sensed impedance values generated by the sensor. The analyzer is configured to detect laryngeal vibrations or cough from the sensed impedance values.

7 Claims, 13 Drawing Sheets

(56) References Cited

U.S. PATENT DOCUMENTS

| | | | |
|---|---|---|---|
| 2005/0119586 A1* | 6/2005 | Coyle et al. | 600/538 |
| 2007/0135725 A1* | 6/2007 | Hatlestad | 600/529 |
| 2008/0051839 A1* | 2/2008 | Libbus et al. | 607/2 |
| 2008/0058874 A1* | 3/2008 | Westlund et al. | 607/2 |
| 2008/0243196 A1 | 10/2008 | Libbus et al. | |
| 2009/0216127 A1* | 8/2009 | Gavriely | 600/453 |
| 2010/0010556 A1 | 1/2010 | Zhao et al. | |
| 2010/0114221 A1 | 5/2010 | Krause et al. | |
| 2010/0191311 A1 | 7/2010 | Scheiner et al. | |
| 2011/0015702 A1 | 1/2011 | Ternes et al. | |
| 2011/0015703 A1 | 1/2011 | Ternes et al. | |
| 2011/0015704 A1 | 1/2011 | Ternes et al. | |
| 2011/0202119 A1* | 8/2011 | Ni et al. | 607/116 |
| 2011/0282416 A1 | 11/2011 | Hamann et al. | |
| 2011/0313488 A1 | 12/2011 | Hincapie Ordonez et al. | |
| 2012/0143286 A1 | 6/2012 | Hahn et al. | |
| 2012/0172741 A1 | 7/2012 | Arcot-Krishnamurthy et al. | |
| 2012/0271382 A1 | 10/2012 | Arcot-Krishnamurthy et al. | |

OTHER PUBLICATIONS

Arcot-Krishnamurthy, Shantha, et al., "Systems and Methods to Account for Neck Movement During Nerve Stimulation", U.S. Appl. No. 61/478,688, filed Apr. 25, 2011, 56 pgs.

Chavan, Abhi V, et al., "Method and Apparatus for Controlling Neurostimulation According to Physical State", U.S. Appl. No. 13/272,786, filed Oct. 13, 2011, 79 pgs.

Hahn, Stephen J, et al., "Systems and Methods for Increasing Stimulation Dose", U.S. Appl. No. 61/420,567, filed Dec. 7, 2010, 40 pgs.

Ordonez, Juan Gabriel Hincapie, et al., "Automatic Neural Stimulation Titration Sweep", U.S. Appl. No. 13/155,549, filed Jun. 8, 2011, 37 pgs.

Ordonez, Juan Gabriel Hincapie, et al., "Systems & Methods to Detect Vagus Capture", U.S. Appl. No. 61/526,568, filed Aug. 23, 2011, 68 pgs.

U.S. Appl. No. 13/309,328, Final Office Action mailed Aug. 27, 2014, 26 pgs.

U.S. Appl. No. 13/309,328, Response filed Mar. 19, 2014 to Non Final Office Action mailed Dec. 23, 2013, 23 pgs.

Japanese Application Serial No. 2013-547488, Office Action mailed Jun. 30, 2014, With English Translation, 2 pgs.

U.S. Appl. No. 13/309,328, Non Final Office Action mailed Dec. 23, 2013, 24 pgs.

International Application Serial No. PCT/US2011/062921, International Preliminary Report on Patentability mailed Jul. 11, 2013, 9 pgs.

International Application Serial No. PCT/US2011/062921, International Search Report mailed May 8, 2012, 4 pgs.

International Application Serial No. PCT/US2011/062921, Written Opinion mailed May 8, 2012, 7 pgs.

U.S. Appl. No. 13/309,328, Advisory Action mailed Nov. 12, 2014, 3 pgs.

U.S. Appl. No. 13/309,328, Non Final Office Action mailed Apr. 8, 2015, 24 pgs.

U.S. Appl. No. 13/309,328, Response filed Jul. 6, 2015 to Non Final Office Action mailed Apr. 8, 2015, 12 pgs.

U.S. Appl. No. 13/309,328, Response filed Oct. 27, 2014 to Final Office Action mailed Oct. 27, 2014, 12 pgs.

Japanese Application Serial No. 2013-547488, Examiners Decision of Final Refusal mailed Feb. 2, 2015, 3 pgs.

\* cited by examiner

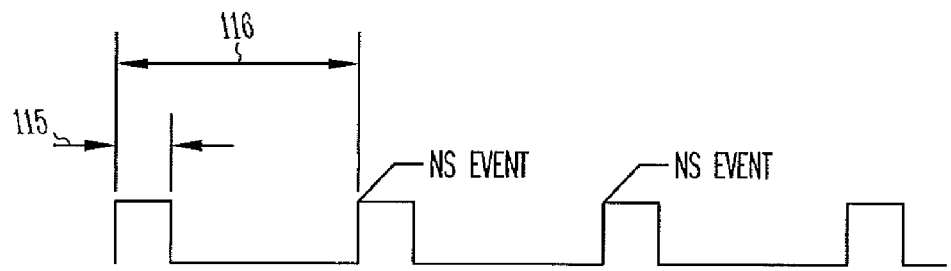
*Fig. 8*
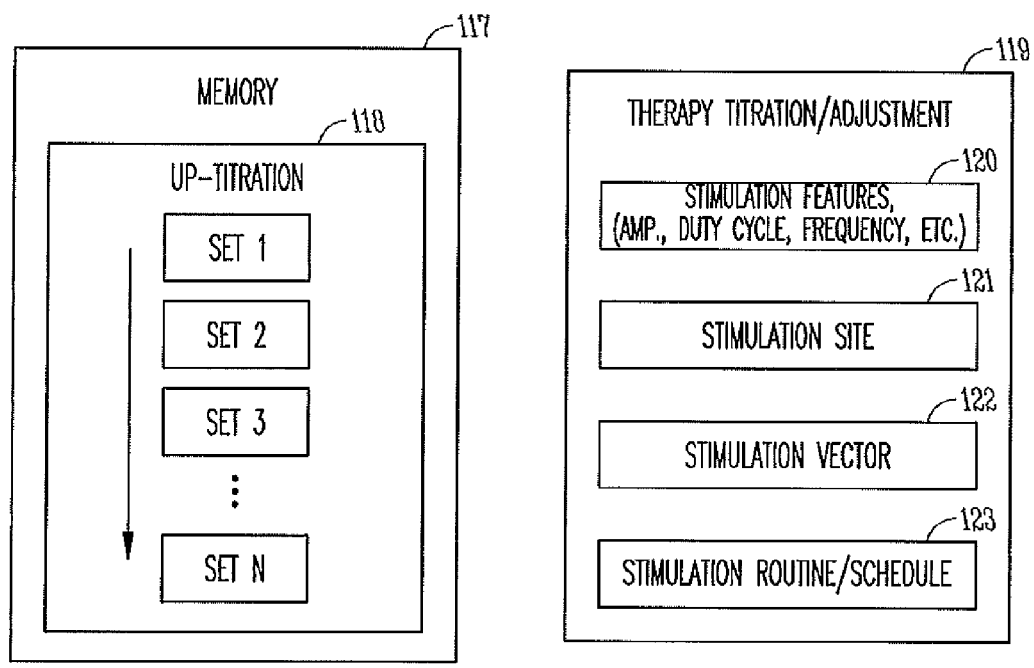
*Fig. 9*          *Fig. 10*

SYSTEMS AND METHODS FOR USING ELECTRICAL IMPEDANCE FOR NEURO CARDIAC THERAPY

CLAIM OF PRIORITY

This application claims the benefit of priority under 35 U.S.C. §119(e) of Arcot-Krishnamurthy et al., U.S. Provisional Patent Application Ser. No. 61/427,978, entitled "SYSTEMS AND METHODS FOR USING ELECTRICAL IMPEDANCE FOR NEURO CARDIAC THERAPY", filed on Dec. 29, 2010, which is herein incorporated by reference in its entirety.

TECHNICAL FIELD

This application relates generally to medical devices and, more particularly, to systems, devices and methods for delivering neural stimulation.

BACKGROUND

Neural stimulation, such as vagus nerve stimulation, has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

SUMMARY

According to an embodiment of a method for detecting laryngeal vibrations, impedance in a cervical region of a patient is sensed to sense changes in impedance characteristics caused by laryngeal vibrations. Sensing impedance includes sensing impedance a plurality of times to provide a plurality of sensed impedance values. The plurality of the sensed impedance values is analyzed to confirm the laryngeal vibrations.

According to an embodiment of a method for detecting cough, impedance in a cervical region of a patient is sensed to sense changes in impedance characteristics caused by cough. Sensing impedance includes sensing impedance a plurality of times to provide a plurality of sensed impedance values. The plurality of the sensed impedance values is analyzed to confirm the cough.

An embodiment of a method includes delivering a vagal stimulation therapy (VST) to the vagus nerve of a patient, and detecting laryngeal vibrations to determine whether the VST is capturing the vagus nerve. Detecting laryngeal vibrations includes sensing impedance in a cervical region of a patient to sense changes in impedance characteristics caused by laryngeal vibrations wherein sensing impedance includes sensing impedance a plurality of times to provide a plurality of sensed impedance values, and analyzing a plurality of the sensed impedance values to confirm the laryngeal vibrations. The values may be analyzed either by itself or by comparison with baseline impedance values collected without any VST.

An embodiment of a method includes performing a threshold determination routine for delivering a vagal stimulation therapy (VST) to a vagus nerve of a patient. Performing the threshold determination routine includes delivering VST to the vagus nerve, changing (increasing or decreasing) an intensity of the VST in a plurality of intensity steps, and at each intensity step monitoring for laryngeal vibrations. Monitoring for laryngeal vibrations includes sensing impedance in a cervical region of a patient to sense impedance changes caused by laryngeal vibrations wherein sensing impedance includes sensing impedance a plurality of times to provide a plurality of sensed impedance values, and analyzing a plurality of the sensed impedance values to confirm the laryngeal vibrations.

A device embodiment is configured to deliver vagal stimulation therapy (VST) to the vagus nerve of a patient. The device embodiment includes a neural stimulator, an implantable impedance sensor and an impedance analyzer. The neural stimulator is configured to deliver the VST to the vagus nerve in the cervical region of the patient. The implantable impedance sensor is configured for use in detecting changes in impedance characteristics in the cervical region of the patient caused by laryngeal vibrations. The impedance sensor is configured to generate sensed impedance values. The impedance analyzer is configured to analyze the sensed impedance values generated by the sensor. The analyzer is configured to detect laryngeal vibrations or cough from the sensed impedance values.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 8 illustrates a representation of intermittent neural stimulation (INS), according to various embodiments.

FIG. 9 illustrates a memory, according to various embodiments, that includes instructions, operable on by the stimulation control circuitry, for controlling an up-titration routine by progressively stepping up through defined parameter sets (e.g. parameter set 1 through parameter set N), where each set incrementally increases the stimulation dose or intensity of the stimulation therapy.

FIG. 10 illustrates an embodiment of a therapy titration module.

DETAILED DESCRIPTION

Figure 1:
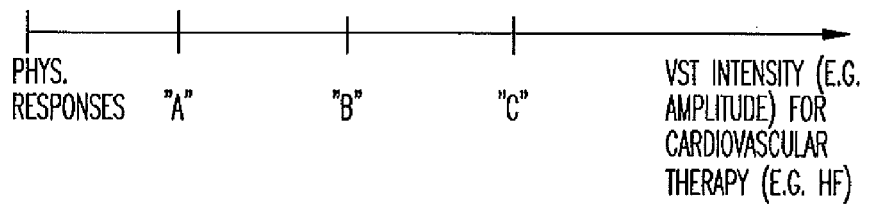
FIG. 1 illustrates intensity thresholds that elicit various physiological responses to VST.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. Some embodiments of the present subject matter can be used to prophylactically or therapeutically treat various cardiovascular diseases by modulating autonomic tone. Neural stimulation to treat cardiovascular diseases is referred to herein as neuro cardiac therapy (NCT). Vagal stimulation used to treat cardiovascular diseases may be termed either VST or NCT. However, VST may be delivered for non-cardiovascular diseases, and NCT may be delivered by stimulating a nerve other than the vagal nerve. Examples of cardiovascular diseases or conditions include HF, hypertension, and cardiac remodeling. These conditions are briefly described below.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

The vagus nerve is a complex physiological structure with many neural pathways that are recruited at different stimulation thresholds. Various physiological responses to vagal stimulation are associated with various thresholds of VST intensity. For example, FIG. 1 illustrates increasing VST intensity from the left side to the right side of the figure, and further illustrates intensity thresholds that elicit various physiological responses to VST. VST causes a physiological response "A" at a lower intensity than an intensity at which VST causes a physiological response "B", which occurs at a lower VST intensity than an intensity at which VST causes a physiological response "C". Stated another way, VST has to reach a certain level before triggering response "A," and has to reach a higher intensity to trigger response "B" along with response "A" and an even higher intensity to trigger response "C" along with responses "A" and "B".

The beneficial effects of VST on cardiac function and remodeling are not necessarily mediated via heart rate reduction. That is, VST can benefit patients without undesired chronotropic effects associated with VST as well as other side effects due to high intensity stimulation such as coughing, muscle stimulation, etc. Rather, anti-inflammatory, anti-sympathetic, and anti-apoptosis mediators are triggered at lower VST intensities than intensities at which a heart rate reduction is realized. These mediators function as pathways through which the VST provides the therapeutic effects for cardiovascular disease.

Physiological responses at the lower VST intensities have therapeutically-effective results for cardiovascular diseases such as HF. These responses mediate or provide pathways for these therapies. Examples of such responses that are beneficial for HF at the lower VST intensities include anti-inflammation, anti-sympathetic, and anti-apoptosis responses, and an increased nitric oxide (NO). Physiological responses at the higher VST intensities may not be desirable. Examples of responses to higher VST intensities that may reduce the ability of the patient to tolerate VST include, but are not limited to, reduced heart rate, prolonged AV conduction, vasodilation, and coughing. At least some of these responses may be desirable for some therapies but not desirable for other therapies. By way of example and not limitation, VST that reduces heart rate and or that prolongs AV conduction may be desirable to treat some cardiovascular diseases, but may not be desirable for other cardiovascular diseases. The intensity of the VST can be adjusted by adjusting parameter(s) of the stimulation signal. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal, a stimulation burst frequency, a pulse width and/or a duty cycle.

Figure 2:
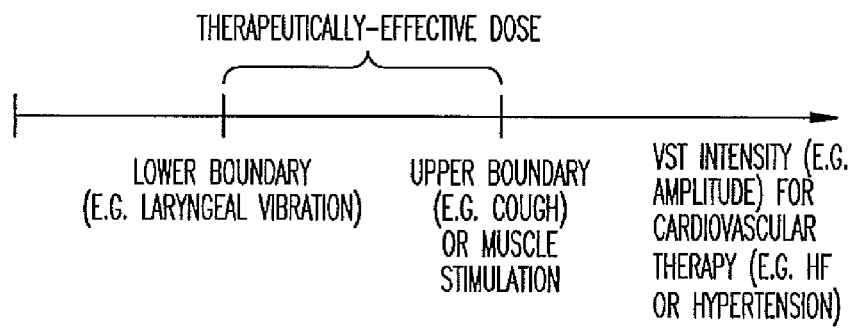
FIG. 2 illustrates au intensity threshold that elicits an undesired physiological response to VST that is used to define an upper boundary for the VST intensity and another intensity threshold that elicits another physiological response to VST, according to various embodiments.

FIG. 2 illustrates increasing VST intensity from the left side to the right side of the figure, and further illustrates an intensity threshold that elicits an undesired physiological response to VST that is used to define an upper boundary for the VST intensity and another intensity threshold that elicits another physiological response to VST. For example, the VST intensity threshold for a cough can be used as an upper boundary, and the VST intensity threshold for a laryngeal vibration response can be used as a lower boundary. In some embodiments, the physiological response to define the upper boundary is a detected muscle stimulation. Large muscle stimulation or extraneous stimulation may be bothersome to the patient. Various embodiments use lead impedance to check for vagus nerve capture that causes the laryngeal nerve to vibrate. Various embodiments use lead impedance to check for cough induced by vagus nerve stimulation. Some embodiments perform impedance-based measurements of laryngeal vibrations without any additional hardware than that which is used by the neurostimulation system.

A vagus nerve capture threshold can be set by first recruiting A fibers that cause laryngeal vibrations, and then increasing the intensity until a cough side effect is detected. The intensity is set between the intensity that caused the laryngeal vibrations and the intensity that caused the cough. For example, if the amplitude of the stimulation signal is increased to increase the VST intensity and if 1 mA caused laryngeal vibrations and 2.5 mA caused a cough, then the pacing amplitude may be set to 2.1 to 2.4 mA. However, determination of thresholds by a physician is time consuming because of the multiple stimulating vectors that are possible. Some embodiments of the present subject matter use a device/ lead based impedance sensor to measure impedance changes caused by laryngeal vibrations and cough to guide the therapy threshold programming. Different versions of an algorithm can be used to provide short term feedback during surgery or to provide relatively long follow-up monitoring.

Figure 3:
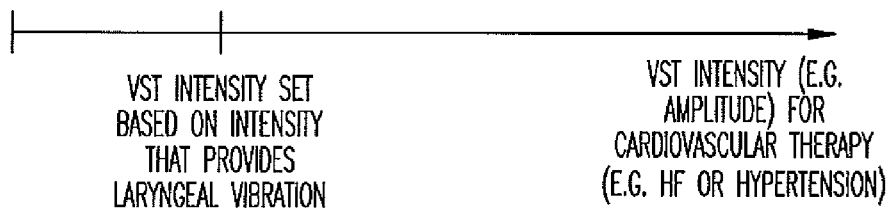
FIG. 3 illustrates that a VST intensity level can be set using the intensity threshold that elicits a physiological response to the VST, according to various embodiments.
Figure 4:
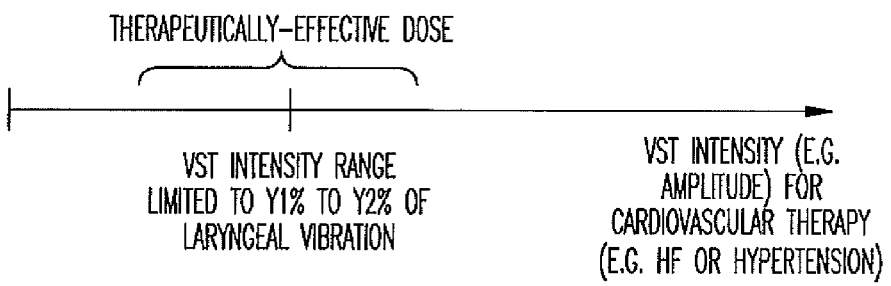
FIG. 4 illustrates using the intensity threshold that elicits a physiological response to set upper and lower limits for a range of VST intensities, according to various embodiments.

FIG. 3 illustrates increasing VST intensity from the left side to the right side of the figure, and further illustrates that a VST intensity level can be set using the intensity threshold that elicits a physiological response to the VST. For example, if laryngeal vibrations are observed at VST intensity level "X", the therapeutically-effective intensity level for the VST can be set as a percentage of "X" (e.g. approximately 75% of "X" or approximately 125% of "X") or as an offset "Z" from "X" (e.g. "X" less "Z" or "X" plus "Z"). As generally illustrated in FIG. 4, the intensity threshold that elicits a physiological response can be used to set upper and lower limits for a range of VST intensities. An ability of the device to adjust the VST intensity range may be limited based on the detected physiological response (e.g. laryngeal vibrations) to the VST. For example, a device may limit adjustments to the VST intensity to Y1% to Y2% of "X" (e.g. 50% to 150% of the laryngeal vibration intensity). By way of example, the lower range may be below and the upper range above 100% of "X", the lower and upper ranges may both be below 100% of "X", or may both be above 100% of "X". Alternatively, offsets ("Z1" and/or "Z2" from "X" (not shown)) may be used for at least one of the beginning of the allowable range of intensities or the end of the allowable range of intensities.

Figure 5:
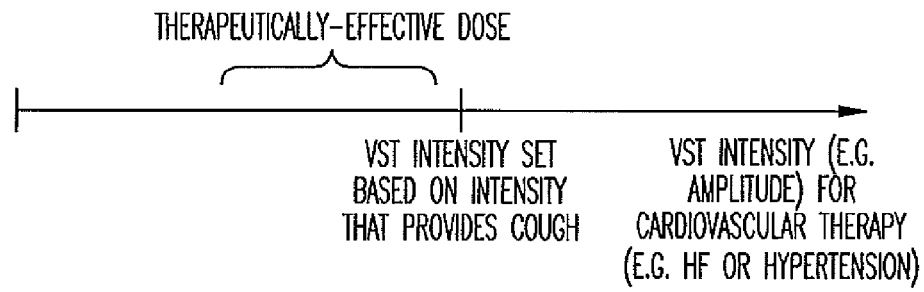
FIG. 5 illustrates the intensity threshold that elicits a physiological response to the VST that is used to set the VST intensity, according to various embodiments.
Figure 6:
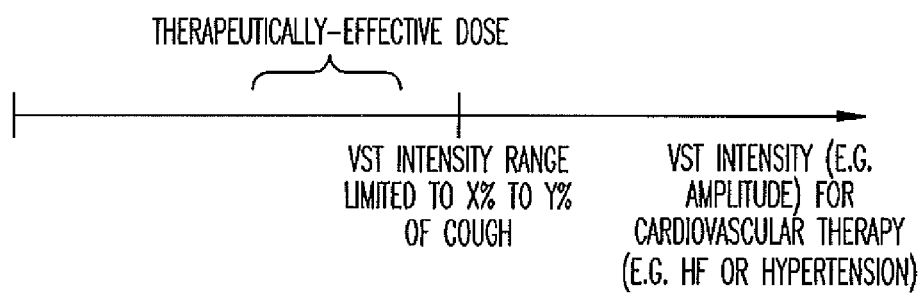
FIG. 6 illustrates using a detected cough response to VST to limit adjustments to the VST intensity range, according to various embodiments.

FIG. 5 illustrates increasing VST intensity from the left side to the right side of the figure, and further illustrates the intensity threshold that elicits a physiological response to the VST that is used to set the VST intensity. For example, if cough is observed the therapeutically-effective intensity level for the VST can be set as a percentage, and offset, or other function of the VST intensity that elicited the cough. As generally illustrated in FIG. 6, an ability of the device to adjust the VST intensity range may be limited based on the detected cough response to VST. For example, a device may limit adjustments to the VST intensity to a range of percentages or other function of the VST intensity that caused the cough ("X"). By way of example, the lower range may be below and the upper range above 100% of "X", the lower and upper boundaries for the range may both be below 100% of "X", or may both be above 100% of "X". It is currently that, for most therapies, both the lower and upper boundaries will be below 100% of "X".

Figure 7:
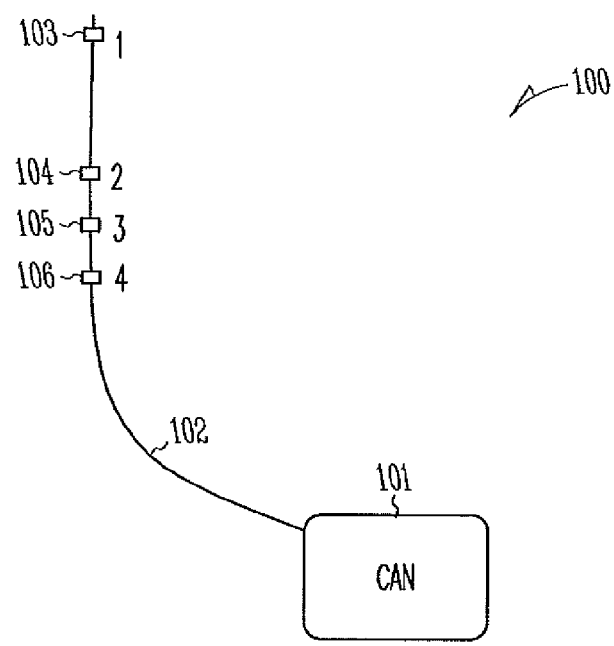
FIG. 7 illustrates an embodiment, by way of example and not limitation, of an implantable medical device capable of measuring impedance with a device housing or can and a lead extending from the can.

FIG. 7 illustrates an embodiment, by way of example and not limitation, of an implantable medical device 100 capable of measuring impedance with a device housing or can 101 and a lead 102 extending from the can. The lead includes multiples poles that can be used in a unipolar configuration or bipolar configuration. The laryngeal vibrations cause the lead and tissue to move with respect to each other, causing the contact between the tissue and the poles to vary and thus causing the impedance to vary. Some poles on the lead can be used to pace, and some embodiments monitor impedance using the poles that are used for pacing. In some embodiments, other poles (other than those used to pace) on the multi-polar lead can be used. In some embodiments, the drive current for the impedance measuring is the neurostimulation current. In some embodiments, a dedicated, sub-therapeutic current is used as the drive current for the impedance measurement. Both AC and DC coupled impedance can be used. Some embodiments use multiple impedance vectors and phase-coherent detection. The impedance sensor can be used in combination with other sensors (accelerometer, strain gauge) and/or patient/physician feedback.

The lead may be an intravascular lead configured to be fed into position through the vasculature of the patient. The lead may be a subcutaneous lead. The lead may be inside or outside the carotid sheath, to provide electrode(s) either adjacent to or surrounding the vagus nerve. The illustrated lead includes four electrodes 103, 104, 105 and 106. However, the present subject matter is not limited to a particular number of electrodes. The can 101 may function as an electrode. In some embodiments, more than one electrode may be on the can 101. Various combinations of the lead electrodes and the can provide various vectors that can be used to calculate impedance between or among these various combinations. Laryngeal vibrations or cough affects the electrode-tissue contact, which affects impedance. Thus, the present subject matter uses impedance as a way to detect laryngeal vibrations and cough. Neural stimulation may be delivered to a nerve, such as the vagus nerve, using at least one of the electrodes on the lead. The current from the neural stimulation may be used to detect the impedance, according to some embodiments. In some embodiments, a dedicated current is used to detect impedance.

Titration, as used herein, refers to the process of adjusting the dose of the stimulation, ultimately to a level that is therapeutically or prophylactically effective. The dose includes an amount or intensity of the neural stimulation at a given time frame, and also includes the number of times the neural stimulation is delivered over a period of time. The intensity of the neural stimulation may be adjusted by adjusting parameters such as amplitude, duty cycle, duration, and or frequency of the neural stimulation, or the number of neural stimulation events that occur over a period of time. FIG. 8 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 115) is delivered, and intervals of stimulation being OFF, when no stimulation pulses are delivered. Thus, for example, some embodiments deliver a plurality of monophasic or biphasic pulses within a neural stimulation burst illustrated in FIG. 8. Pulses delivered within a burst 115 may be delivered at a pulse frequency. These pulses also have an amplitude. Both the pulse frequency and the pulse amplitude affect the dose of the neural stimulation therapy. The duration of the stimulation ON interval is sometimes referred to as the stimulation duration or burst duration. The burst duration also affects the dose of the neural stimulation therapy. The start of a stimulation ON interval is a temporal reference point NS Event. The time interval between successive NS Events is the INS Interval, which is sometimes referred to as the stimulation period or burst period 116. The burst period 116 or the number of neural stimulation events that occur over a time period also affect the dose of the neural stimulation. For an application of neural stimulation to be intermittent, the stimulation duration (i.e., ON interval) is less than the stimulation period (i.e., INS Interval) when the neural stimulation is being applied. The duration of the OFF intervals of INS are determined by the durations of the ON interval and the INS Interval. The duration of the ON interval relative to the INS Interval (e.g., expressed as a ratio) is sometimes referred to as the duty cycle of the INS.

FIG. 9 illustrates a memory 117, according to various embodiments, that includes instructions 118, operable on by the stimulation control circuitry, for controlling an up-titration routine by progressively stepping up through defined parameter sets (e.g. parameter set 1 through parameter set N), where each set incrementally changes (increases or decreases) the stimulation dose or intensity of the stimulation therapy. This memory may be illustrated as part of a therapy titration/adjustment module 119 in FIG. 10. The memory may include a plurality of neural stimulation parameter sets, where each set includes a unique combination of parameter values for the neural stimulation and wherein each unique combination of parameter values is defined to provide neural stimulation therapy at an intensity level. The instructions include instructions for stepping through the plurality of neural stimulation parameter sets according to a schedule to change (increase or decrease) the intensity of the therapy until the therapy is at the desired long term intensity. Various embodiments provide a neural stimulation routine that automatically finds the desirable combination of therapy parameters (e.g. amplitude, pulse width, duty cycle) that provides a desired therapy intensity level.

FIG. 10 illustrates an embodiment of a therapy titration module 119, which may also be referred to as a therapy adjustment module. According to various embodiments, the stimulation control circuit is adapted to set or adjust any one or any combination of stimulation features 120. Examples of stimulation features include the amplitude, frequency, polarity and wave morphology of the stimulation signal. Examples of wave morphology include a square wave, triangle wave, sinusoidal wave, and waves with desired harmonic components to mimic naturally-occurring baroreflex stimulation. Some embodiments of the stimulation output circuit are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The therapy titration module 119, also referred to as a therapy adjustment module, can be programmed to change stimulation sites 121, such as changing the stimulation electrodes used for a neural target or changing the neural targets for the neural stimulation. For example, different electrodes of a multi-electrode cuff can be used to stimulate a neural target. Examples of neural targets include the right and left vagus nerves and branches thereof, baroreceptors, the carotid sinus, and the carotid sinus nerve. Autonomic neural targets can include afferent pathways and efferent pathways and can include sympathetic and parasympathetic nerves. The stimulation can include stimulation to stimulate neural traffic or stimulation to inhibit neural traffic. Thus, stimulation to evoke a sympathetic response can involve sympathetic stimulation and/or parasympathetic inhibition; and stimulation to evoke a parasympathetic response can involve parasympathetic stimulation and/or sympathetic inhibition.

The therapy titration module 119 can be programmed to change stimulation vectors 122. Vectors can include stimulation vectors between electrodes, or stimulation vectors for transducers. For example, the stimulation vector between two electrodes can be reversed. One potential application for reversing stimulation vectors includes changing from stimulating neural activity at the neural target to inhibiting neural activity at the neural target. More complicated combinations of electrodes can be used to provide more potential stimulation vectors between or among electrodes. One potential stimulation vector application involves selective neural stimulation (e.g. selective stimulation of some axons of the vagus nerve) or changing between a selective stimulation and a more general stimulation of a nerve trunk.

The therapy titration module 119 can be programmed to control the neural stimulation according to stimulation instructions, such as a stimulation routine or schedule 123, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit can be programmable. The controller may also terminate a neural stimulation session in response to an interrupt signal, such as may be generated by one or more sensed parameters or any other condition where it is determined to be desirable to stop neural stimulation.

A device may include a programmed therapy schedule or routine stored in memory and may further include a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

According to various embodiments, the stimulation schedule refers to the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2 AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, a particular position/posture, low heart rate levels, and the like. For example, the stimulation can be synchronized to the cardiac cycle based on detected events that enable the stimulation. The therapy schedule can also specify how the stimulation is delivered.

Some embodiments are configured to change a ramp-up time for increasing one or more stimulation parameters from OFF to a programmed intensity at the start of the ON portion. Patients may tolerate higher stimulation levels if there is not an abrupt change at the start of the duty cycle. The parameter increased during this ramp-up time may be amplitude, for example, or other parameter or other combination of parameters that affect the intensity of the stimulation.

Figure 11:
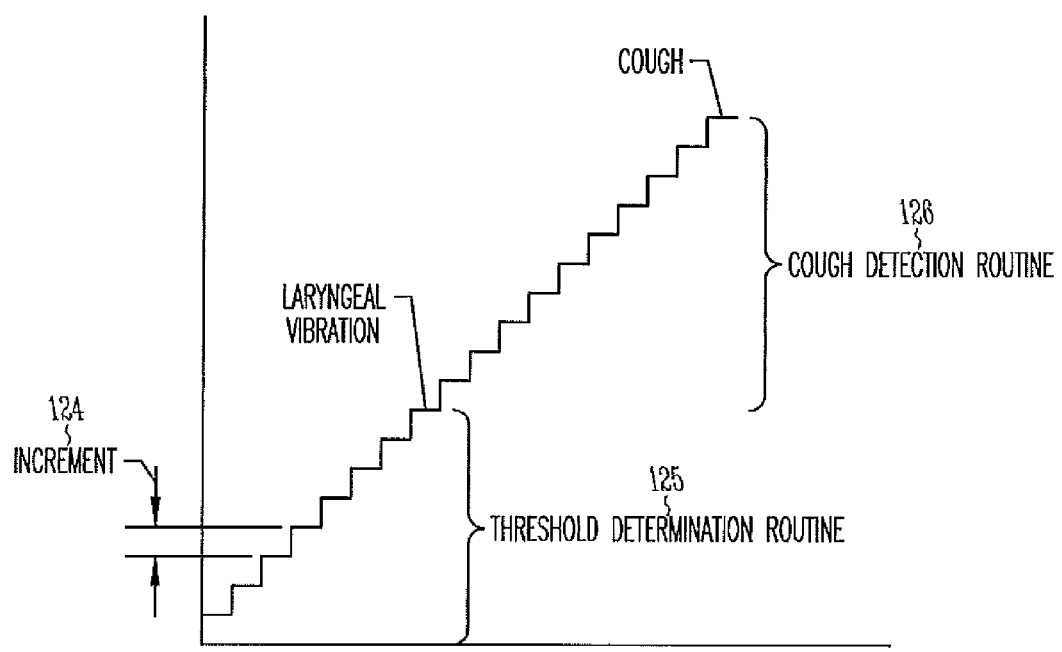
FIG. 11 illustrates an embodiment of a routine that increases the intensity of the NCT therapy over a period of time.

FIG. 11 illustrates an embodiment of a routine that increases the intensity of the NCT therapy over a period of time. The intensity is increased in increments 124. In the illustrated embodiments, a threshold determination routine 125 is performed to detect a lower boundary physiologic response to the neural stimulation such as a laryngeal vibration response. In various embodiments, a cough detection routine 126 or other side effect detection routine is performed to detect an upper boundary physiologic response to the neural stimulation. Some embodiments decrease the intensity of the NCT therapy over a period of time to detect the physiologic responses (e.g. lower and/or upper boundaries) to the neural stimulation.

The present subject matter senses physiological responses using an impedance sensor configured to sense impedance changes caused by the physiological response to the neural stimulation. As a specific example, some embodiments sense changes in impedance characteristics caused by laryngeal vibrations, and some embodiments sense changes in impedance characteristics caused by cough. By way of example and not limitation, the laryngeal vibrations and cough can be used to determine lower and upper boundaries for the NCT. The impedance is sensed a plurality of times to provide a plurality of sensed impedance values. A plurality of the sensed impedance values is analyzed to confirm the laryngeal vibrations. Some embodiments position the impedance sensor extravascularly in or proximate to the carotid sheath in a position to allow the sensor to sense changes in impedance characteristics caused by laryngeal vibrations. Some embodiments position the impedance sensor intravascularly in or proximate to the carotid sheath to allow the sensor to sense changes in impedance characteristics caused by laryngeal vibrations.

Figure 12A:
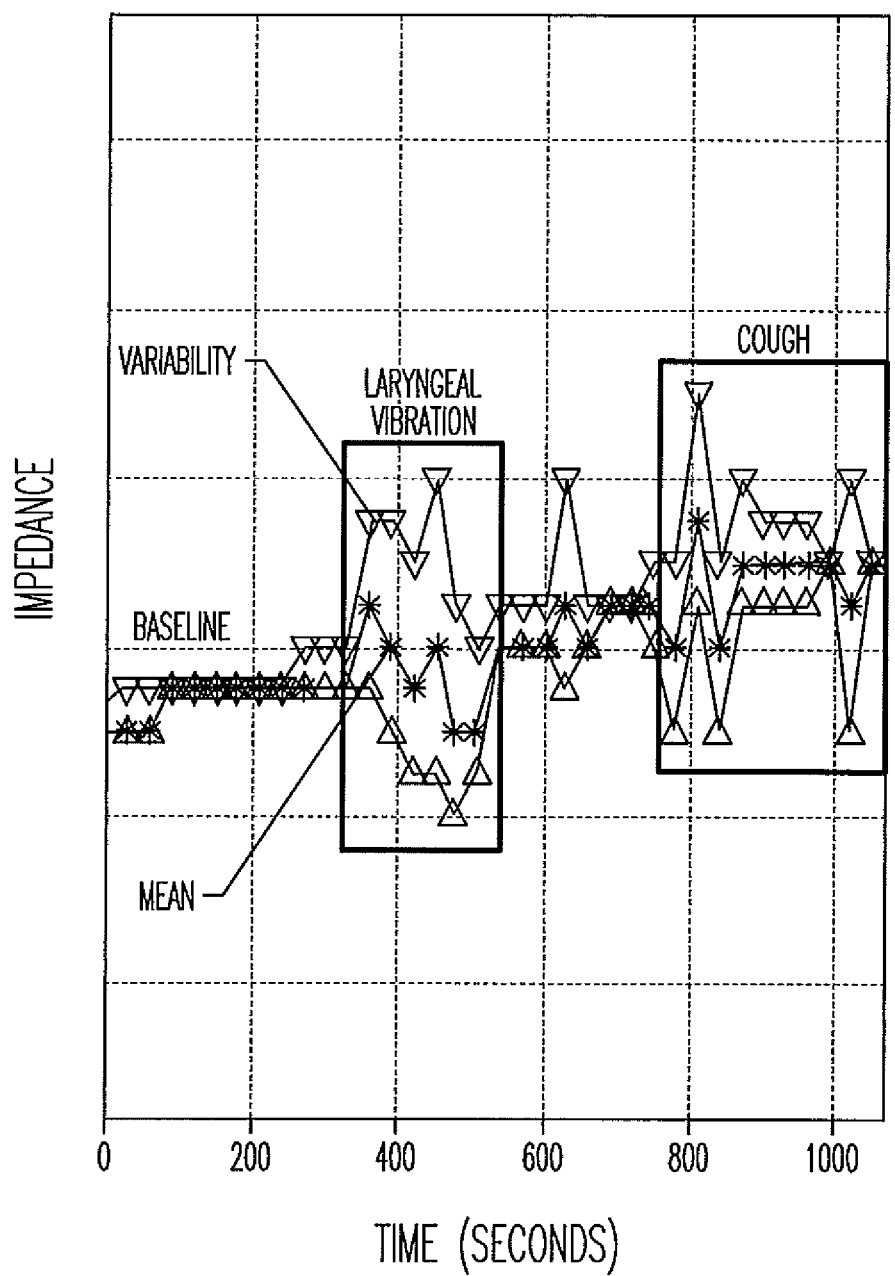
FIGS. 12A and 12B illustrate, by way of example, impedance measurements such as may be sensed according to the present subject matter.

FIG. 12A illustrates, by way of example, impedance measurements. The illustrated figure represents a baseline, an area with an increased mean and variability representing laryngeal vibrations, and an area with a further increase in the mean and variability representing cough. Discrimination algorithms can be used to detect laryngeal vibrations and cough from the sensed impedance values. Some embodiments provide discrimination algorithms to detect muscle stimulation. Large muscle stimulation is expected to look similar to cough.

Figure 12B:
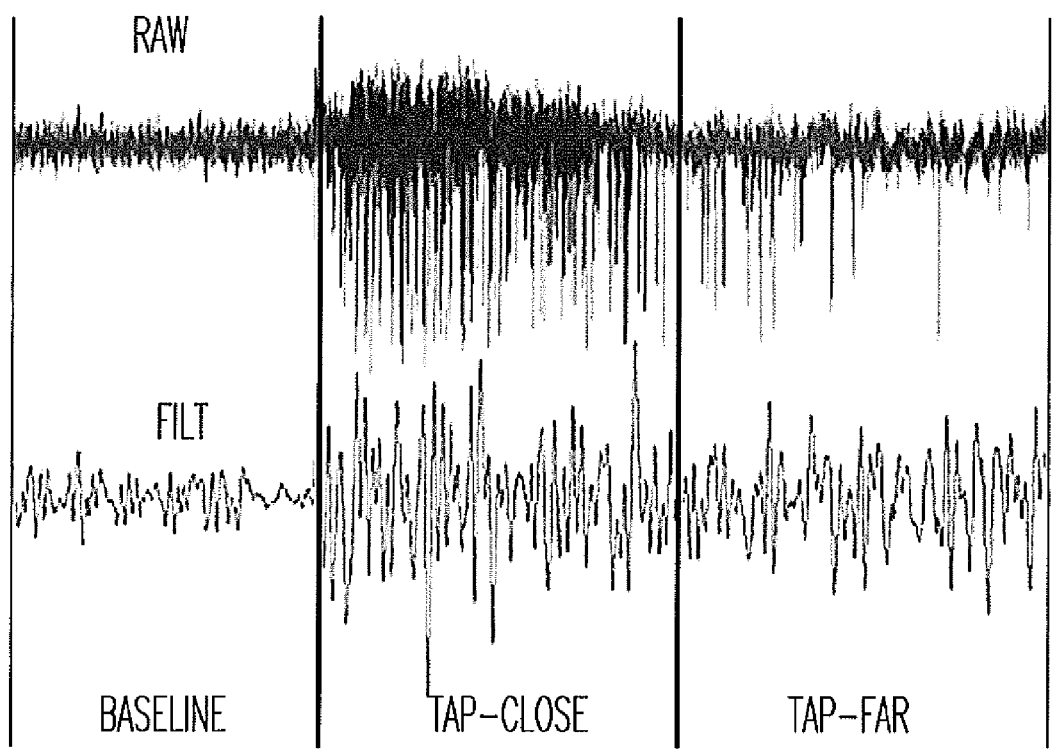

FIG. 12B illustrates both raw and filtered impedance measurements when a patient is tapped close to the impedance sensor and when the patient is tapped further away from the impedance sensor. Similar to FIG. 12A, a variability measure of the impedance values will indicate the presence of laryngeal vibrations and cough. The first step change in impedance variability will reflect the presence of laryngeal vibrations (compared to baseline) and the second step change (if present) may reflect the presence of cough or muscle stimulation (compared to laryngeal vibrations). The figure indicates that the variability measure depends on the location of the sensor relative to the origin of the laryngeal vibrations.

Figure 14:
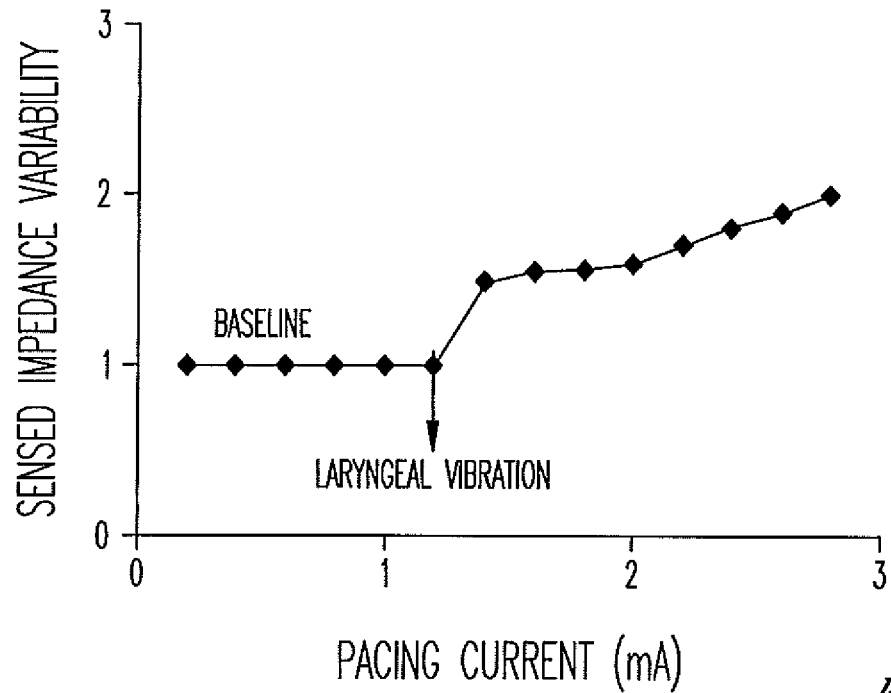
FIG. 14 illustrates a step up in the variability of the sensed impedance when laryngeal vibrations occur and FIG. 15 illustrates a step up in the variability of the sensed impedance when cough occurs, which are detected according to various embodiments of the present subject matter.
Figure 15:
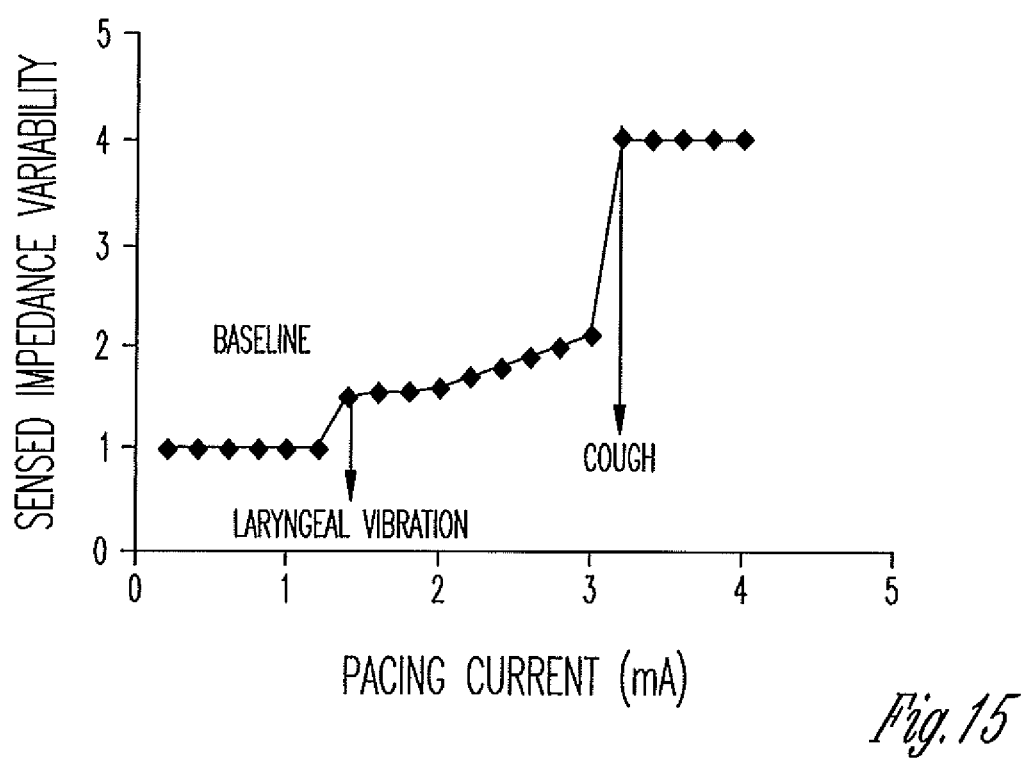

Various embodiments analyze a plurality of sensed impedance values to detect physiological responses to the NCT, such as laryngeal vibrations and/or cough. Some embodiments correlate the timing of the neural stimulation bursts to the timing of the physiological responses to determine whether the physiological response is attributable to the NCT. According to various embodiments, the physiological response is detected by detecting a change in impedance characteristics (e.g. detecting a change in absolute impedance values, detecting a change in a mean of the sensed impedance values, and/or detecting a change in variability of the sensed impedance values). FIG. 14 illustrates a step up in the variability of the sensed impedance when laryngeal vibrations occur. FIG. 15 illustrates a step up in the variability of the sensed impedance when cough occurs. By way of example and not limitation, some system embodiments monitor a trend of the variability of the sensed impedance as the intensity is increased and detects the physiological response if the trend changes by more than threshold.

Figure 13A:
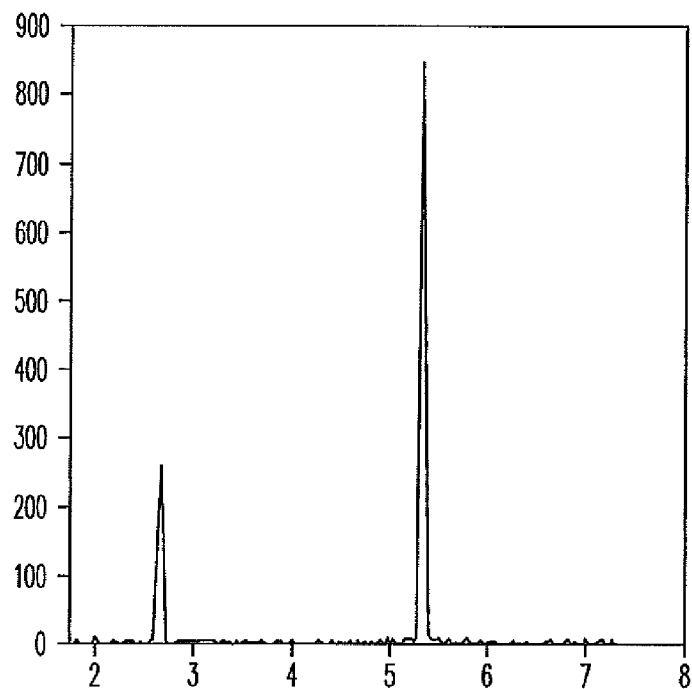
FIG. 13A illustrates the frequency transformation of the vagal stimulation pulses delivered at 160 beats per minute where the two peaks in frequencies are at 2.6 and 5.2 Hz respectively.
Figure 13B:
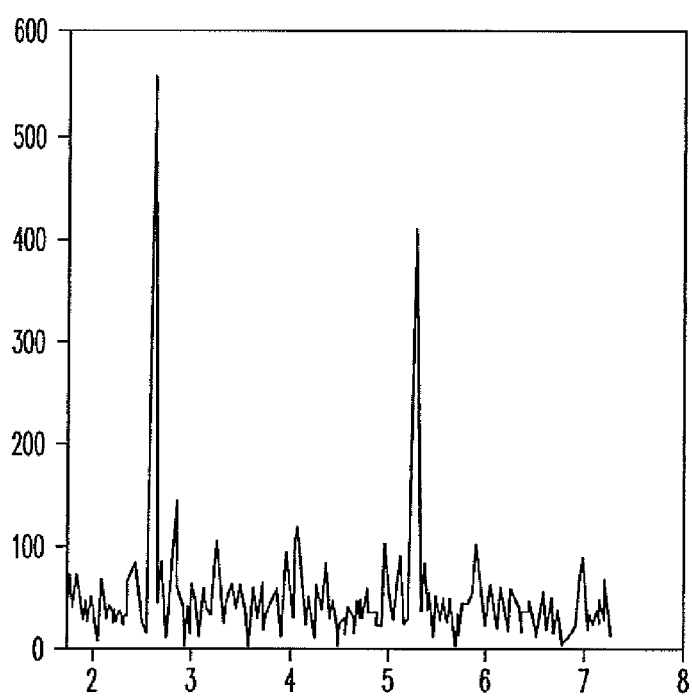
FIG. 13 B illustrates the frequency transformation of the impedance signal collected during the vagal stimulation where the two primary peaks are again at 2.6 Hz and 5.2 Hz, thus verifying capture by corresponding to the peak frequencies of the vagal stimulation pulses.

FIG. 13A illustrates the frequency transformation of the vagal stimulation pulses delivered at 160 beats per minute where the two peaks in frequencies are at 2.6 and 5.2 Hz respectively. The 5.2 Hz frequency peak represents the second harmonic of 2.6 Hz. FIG. 13 B illustrates the frequency transformation of the impedance signal collected during the vagal stimulation where the two primary peaks are again at 2.6 Hz and 5.2 Hz, thus verifying capture by corresponding to the peak frequencies of the vagal stimulation pulses. Thus, some embodiments perform frequency analysis on the stimulation and on the sensed impedance to determine if the sensed impedance is affected by the stimulation. If the sensed impedance has a frequency response that compares favorably (e.g. peak-to-peak comparison) to the frequency response of the stimulation, then it can be concluded that the stimulation is affecting the impedance response. Thus, the frequency analysis indicates capture. Various embodiments incorporate the impedance sensor in the lead and/or the can. Some embodiments incorporate the impedance sensor into the lead or other temporary guide catheters for use during implant. Some embodiments use impedance sensor(s) with other sensors such as a pressure sensor and/or accelerometer, and/or use patient or physician feedback.

Various embodiments of the present subject matter provide a programmed process used during implant. A baseline measure of impedance is obtained with multiple vectors, and the stimulation is delivered with the intensity of the stimulation increased in steps. Some embodiments decrease the intensity of the stimulation in steps. The stimulation is delivered for a known time period at each setting. Impedance measurements are made for each pre-set time window. Some embodiments use phase-coherent detection to provide frequency filtering. The impedance measurements are analyzed. Some embodiments calculate a measure of impedance measurement variability. Examples of methods that may be used include calculating standard deviation, a range, Or an Inter-Percentile Range such as an Inter Quartile Range (IQR). Some embodiments calculate a measure of impedance measurement average. Examples of methods that may be used include calculating a mean or a median. The first step change is determined to be the start of laryngeal vibrations. The intensity where laryngeal vibrations start is used in a function to provide a threshold and set the stimulation intensity. Lead re-positioning is recommended if the threshold is high. The determined stimulation threshold is recorded.

Various embodiments of the present subject matter provide a programmed process used during a follow up. The impedance sensor is used to obtain a baseline measure, and the stimulation is delivered with the intensity of the stimulation increased in steps. The stimulation is delivered for a known time period at each setting. Impedance measurements are made for each pre-set time window. Some embodiments use phase-coherent detection to provide frequency filtering. Some embodiments use the change in impedance characteristics after the delivery of the VST pulse and look in a certain time window after the delivery of the VST pulse. Typically the laryngeal vibrations occur after a short time interval (~10 ms) after the delivery of the VST in the cervical region. Thus we would look for changes in impedance characteristics, after the delivery of each VST pulse, following a certain time window. The impedance measurements are analyzed. Some embodiments calculate a measure of impedance measurement variability. Examples of methods that may be used include calculating standard deviation, a range, or an Inter-Percentile Range such as an Inter Quartile Range (IQR). Some embodiments calculate a measure of impedance measurement average. Examples of methods that may be used include calculating a mean or a median. The first step change is determined to be the start of laryngeal vibrations. The intensity where laryngeal vibrations start is used in a function to provide a threshold. For example, if laryngeal vibrations are sensed at 1 MA, the intensity threshold can be set to 2 mA. A second step change can be used to detect cough. For example, if cough occurs at 3.2 mA, the threshold can be set at 3 mA. If the threshold is too high during implant or follow-up, lead repositioning, both physical repositioning and electronic repositioning, may be recommended. Some embodiments perform an automatic stimulation threshold determination and an automatic stimulation capture confirmation. Some embodiments perform the automatic routine on a beat-to-beat basis, e.g., performing that after each stimulus. Some embodiments perform periodic follow-up of thresholds to monitor for lead/electrode migration, lead/electrode status, monitoring of healing. Some embodiments temporarily turn off the NCT or reduce the intensity of the NCT if a string of coughing is detected.

Various embodiments of the present subject matter provide a programmed process used for therapy verification. Laryngeal vibration capture is checked intermittently such as, by way of example and not limitation, using a programmed schedule or periodically checked every 6 hours, 12 hours, daily, weekly. Some embodiments check laryngeal vibration capture on demand. For example, users may manually request a check for laryngeal vibration capture. Each time laryngeal vibration capture is checked, a plurality of impedance values are sensed and analyzed. The presence or absence of laryngeal vibrations is logged and tracked. A therapy setting is modified if capture is continuously absent. If the highest setting does not cause laryngeal vibrations, a notification is sent or an alert issued. If capture is periodically present, a histogram can be generated to convey how many measurements, or a percentage of measurements, where capture was present along with time-stamps. A message, such as "Therapy was delivered 50% of the time", can be displayed or otherwise communicated.

Figure 16:
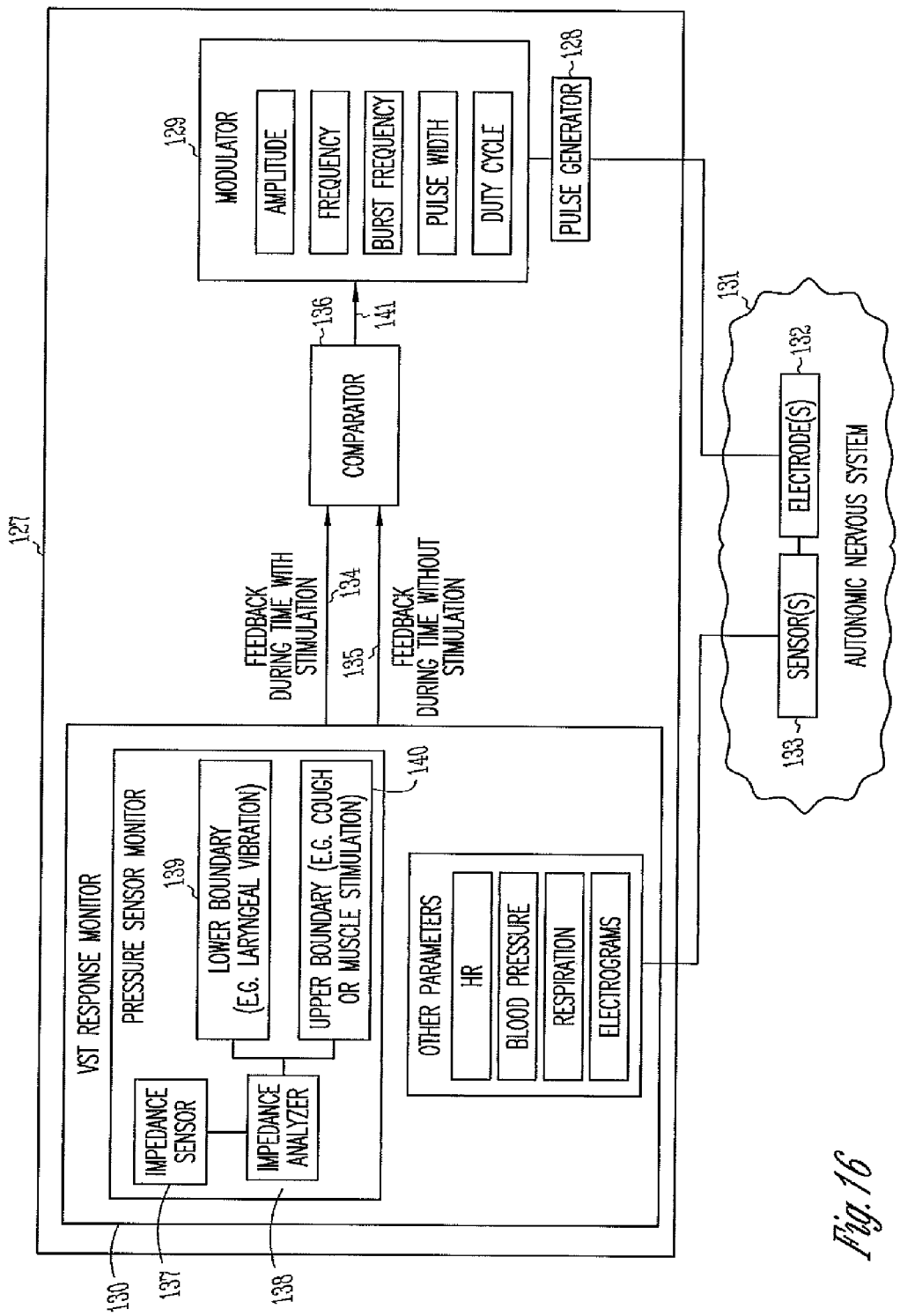
FIG. 16 illustrates a VST system, according to various embodiments.

FIG. 16 illustrates a VST system, according to various embodiments. An implantable device may provide the entire VST system. Some embodiments use external devices to provide the monitoring functions, such as during implantation of an implantable vagus nerve stimulator. Some embodiments use implanted leads and external stimulators. The illustrated VST system 127 includes a pulse generator 128 to provide VST, a modulator 129 to change or modulate intensity of the VST, and a VST response monitor 130 to provide feedback. The autonomic nervous system is generally illustrated at 131. Appropriate electrode(s) 132 are used to provide desired neural stimulation and sensor(s) 133 to sense a parameter that is affected by the neural stimulation. Physiological parameter(s) that quickly respond to VST can be used in closed loop systems or during the implantation process. Examples of such parameters include heart rate, laryngeal vibrations, blood pressure, respiration, and electrogram parameters. The present subject uses an impedance sensor to detect laryngeal vibrations or cough caused by NCT. Other cardiovascular parameter(s) and other surrogate parameters that have a quick and predictable response indicative of the overall response of the parasympathetic nervous system to the neural stimulation can be used. Other parameter(s) that have a slower response may be used to confirm that a therapeutically-effective dose is being delivered. The sensor(s) and electrode(s) can be integrated on a single lead or can use multiple leads. Additionally, various system embodiments implement the functions using an implantable neural stimulator capable of communicating with a distinct or integrated implantable cardiac rhythm management device.

The illustrated response monitor 130 monitors the parameter during a time with stimulation to provide a first feedback signal 134 indicative of a parameter value corresponding to a time with stimulation and during a time without stimulation to provide a second feedback signal 135 indicative of a parameter value corresponding to a time without stimulation. The signals 134 and 135 are illustrated as separate lines. These signals 134 and 135 can be sent over different signal paths or over the same signal path. A comparator 136 receives the first and second feedback signals 134 and 135 and determines a detected change in the parameter value based on these signals. Additionally, the comparator compares the detected change with an allowed change, which can be programmed into the device. For example, the device can be programmed to allow a heart rate reduction during VST to be no less than a percentage (e.g. on the order of 95%) of heart rate without stimulation. The device may be programmed with a quantitative value to allow a heart rate reduction during VST to be no less than that quantitative value (e.g. 5 beats per minute) than heart rate without stimulation. A comparison of the detected change (based on signals 134 and 135) and the allowed change provide a comparison result 141, which is used to appropriately control the modulator to adjust the applied VST.

The illustrated device includes an impedance sensor 137 and an impedance analyzer 138 such as, by way of example and not limitation, an impedance variability analyzer or frequency analyzer. The analyzer analyzes a plurality of sensed impedance values to determine if the laryngeal vibrations and/or cough is caused by the neural stimulation. The device is programmed with an upper boundary value 140 such as may represent a cough and a lower boundary 139 such as may represent laryngeal vibrations. The output of the impedance analyzer 138 is compared to the lower and upper boundaries to determine if the VST intensity is out of bounds.

Some embodiments use a therapy protocol that adjusts the VST intensity, limited by the upper boundary for the VST intensity and in some embodiments by the lower boundary for the VST intensity. The VST intensity can be adjusted, within the allowed bounds set by the present subject matter, based on other parameters such as blood pressure, respiration, and electrogram measurement. Some therapy protocols adjust the upper boundary and/or lower boundary for VST intensity based on a schedule (e.g. time of day) or sensed data (e.g. activity).

Various modulator embodiments adjust VST intensity by changing an amplitude of a stimulation signal used to provide VST, by changing a frequency of a stimulation signal used to provide VST, by changing a burst frequency of a stimulation signal used to provide VST, by changing a pulse width of a stimulation signal used to provide VST, by changing a duty cycle of a stimulation signal used to provide VST, or various combinations of two or more of these stimulation signal characteristics.

The illustrated system for delivering VST is useful in extended therapy applications. Examples of extended therapy applications involve applying stimulation to prevent remodeling of cardiac tissue and to reverse remodel cardiac tissue in cardiovascular disease. VST can be applied for a portion (approximately 10 seconds) of each minute, for example. A VST dose may be adjusted by adjusting the duration or duty cycle of the stimulation (e.g. approximately 5 seconds or 15 seconds each minute or approximately 5 to 15 seconds every 30 seconds or approximately 5 to 30 seconds every 2 minutes, or approximately 5 seconds to 3 minutes every 5 minutes or a continuous stimulation). According to an embodiment, the VST non-selectively stimulates both efferent and afferent axons. The illustrated values are provided by way of example, and not limitation. Over the course of days, weeks, months and years, the physiological response to VST can vary for a number of reasons, such as nerve adaptation, tissue encapsulation, fibrosis, impedance changes, and the like. Various closed loop system embodiments monitor at least one parameter that has a quick and predictable response to VST, and uses the monitored parameter to appropriately change the neural stimulation signal to result in a desired stimulation of the parasympathetic nervous system. Some embodiments monitor heart rate. Some embodiments monitor laryngeal vibrations, and adjust VST intensity as necessary for the VST to elicit laryngeal vibrations.

Open loop VST systems set the VST intensity to avoid or reduce heart rate effects of VST. For an open loop VST system, heart rate is monitored during VST testing. This VST testing may be based on a relatively large human population to determine the heart rate threshold. The VST testing may also be performed during the implantation procedure, using a process that verifies capture of the vagus nerve using observed heart rate reduction, that determines the intensity threshold at which the heart rate reduction is observed, and that uses the intensity threshold to provide an upper boundary or otherwise set the VST intensity below the heart rate threshold. According to some embodiments, a lower boundary for the VST intensity can be set during the implantation process. For example, laryngeal vibrations are felt by the patient or sensed by a sensor such as an accelerometer at a VST intensity level below the VST intensity level where a heart rate effect is detected. A combination of parameter settings is chosen to avoid any significant bradycardia effects. Some embodiments avoid any bradycardia effects. Some embodiments allow a relatively insignificant amount of heart rate slowing (e.g. heart rate during VST at 95% of heart rate without VST). The upper boundary for the VST intensity is based on the allowed heart rate change caused by VST from the intrinsic heart rate without VST.

Figure 17:
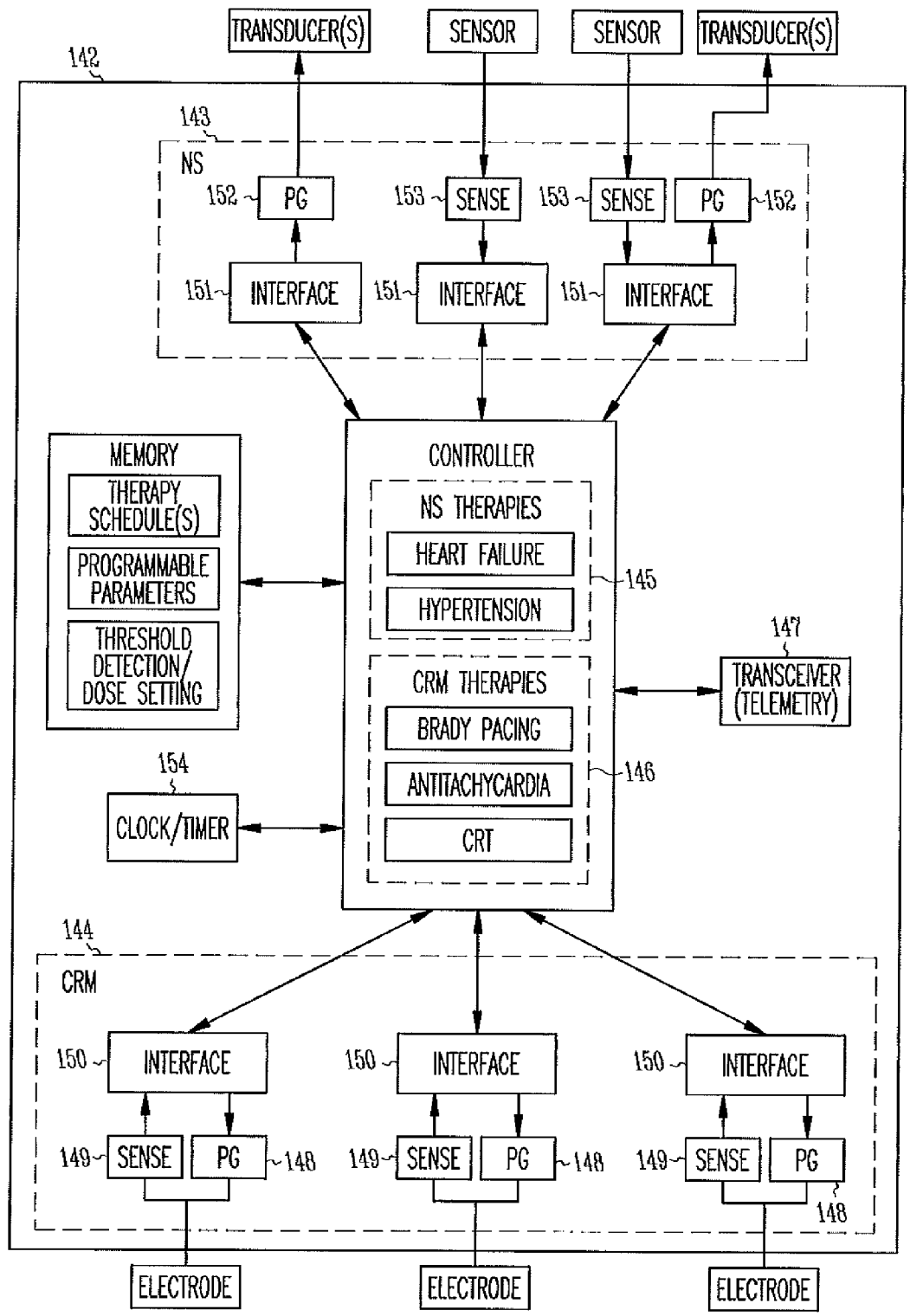
FIG. 17 illustrates an implantable medical device (IMD) having a neural stimulation (NS) component and a cardiac rhythm management (CRM) component according to various embodiments of the present subject matter.

FIG. 17 illustrates an implantable medical device (IMD) 142 having a neural stimulation (NS) component 143 and a cardiac rhythm management (CRM) component 144 according to various embodiments of the present subject matter. The illustrated device includes a controller and memory. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, therapy schedule(s), programmable parameters and threshold detection or dose setting algorithms such as disclosed herein can be stored in memory. Additionally, some embodiments store a threshold detection routine for detecting a threshold for the neural stimulation, and some embodiments store a dose setting routine for titrating the dose. According to various embodiments, the controller includes a processor to execute instructions embedded in memory to perform the neural stimulation and CRM functions. The illustrated neural stimulation therapy 145 can include VST, such as VST to treat heart failure or other cardiovascular disease. Various embodiments include CRM therapies 146, such as bradycardia pacing, anti-tachycardia therapies such as ATP, defibrillation and cardioversion, and cardiac resynchronization therapy (CRT). The illustrated device further includes a transceiver 147 and associated circuitry for use to communicate with a programmer or another external or internal device. Various embodiments include a telemetry coil.

The CRM therapy component 144 includes components, under the control of the controller, to stimulate a heart and/or sense cardiac signals using one or more electrodes. The illustrated CRM therapy section includes a pulse generator 148 for use to provide an electrical signal through an electrode to stimulate a heart, and further includes sense circuitry 149 to detect and process sensed cardiac signals. An interface 150 is generally illustrated for use to communicate between the controller 143 and the pulse generator 148 and sense circuitry 149. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy component 143 includes components, under the control of the controller, to stimulate a neural stimulation target and/or sense parameters associated with nerve activity or surrogates of nerve activity such as heart rate, blood pressure, respiration. Three interfaces 151 are illustrated for use to provide neural stimulation. However, the present subject matter is not limited to a particular number interfaces, or to any particular stimulating or sensing functions. Pulse generators 152 are used to provide electrical pulses to transducer/electrode or transducers/electrodes for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 153 are used to detect and process signals from a sensor, such as a sensor of nerve activity, heart rate, blood pressure, respiration, and the like. Sensor(s) may be used to sense laryngeal vibrations. Sensor(s) may be used to detect a state (e.g. accelerometer used to detect activity). The interfaces 151 are generally illustrated for use to communicate between the controller 143 and the pulse generator 152 and sense circuitry 153. Each interface, for example, may be used to control a separate lead. Various embodiments of the NS therapy section only include a pulse generator to stimulate a neural target. The illustrated device further includes a clock/timer 154, which can be used to deliver the programmed therapy according to a programmed stimulation protocol and/or schedule.

Figure 18:
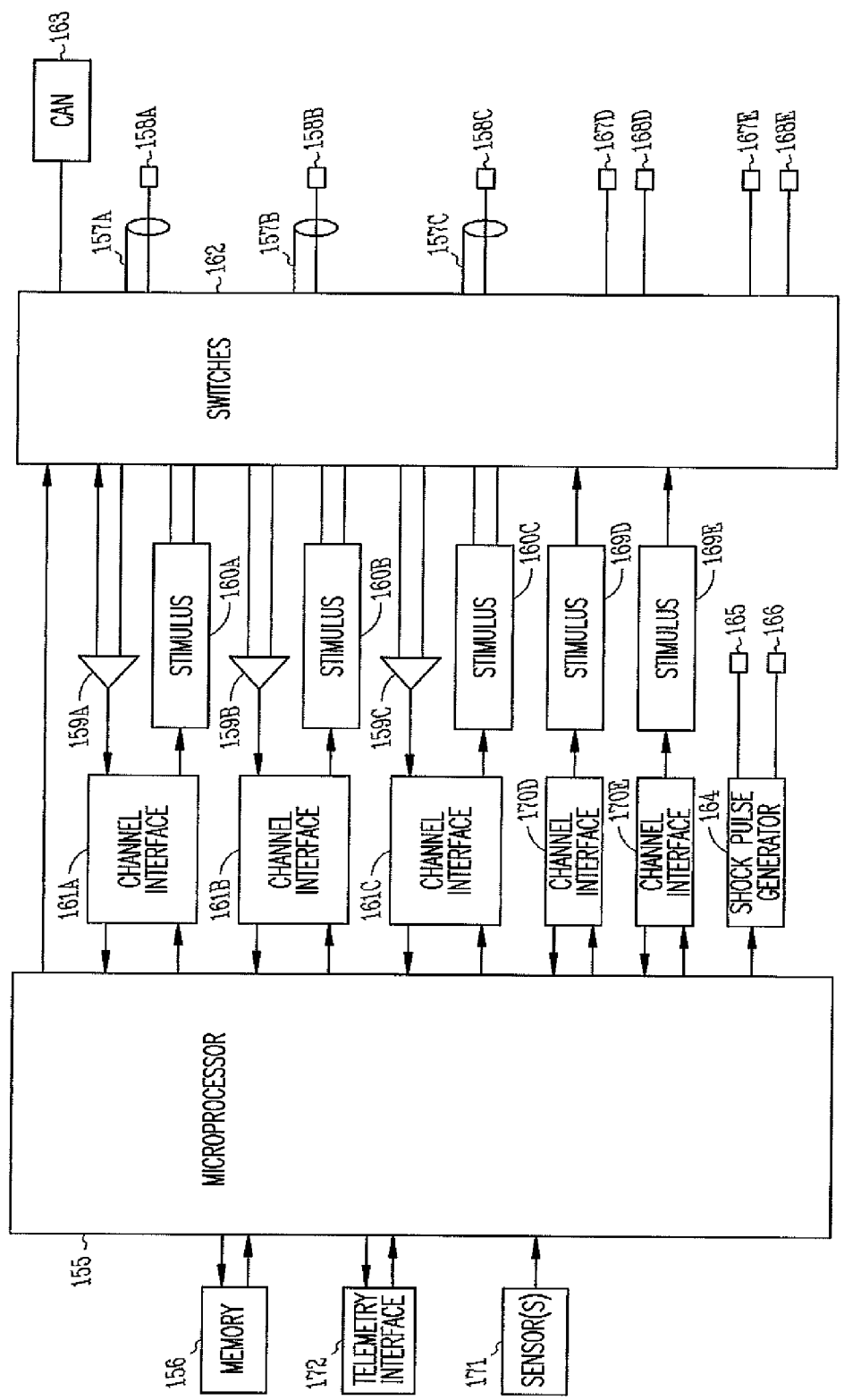
FIG. 18 shows a system diagram of an embodiment of a microprocessor-based implantable device, according to various embodiments.

FIG. 18 shows a system diagram of an embodiment of a microprocessor-based implantable device, according to various embodiments. The controller of the device is a microprocessor 155 which communicates with a memory 156 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 157A-C and tip electrodes 158A-C, sensing amplifiers 159A-C, pacing stimuli 160A-C, and channel interfaces 161A-C. Each channel thus includes a pacing channel made up of the pulse generator connected to the electrode and a sensing channel made up of the sense amplifier connected to the electrode. The channel interfaces 161A-C communicate bidirectionally with the microprocessor 155, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 162 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 163 or au electrode on another lead serving as a ground electrode. A shock pulse generator 164 is also interfaced to the controller for delivering a defibrillation shock via shock electrodes (e.g. electrodes 165 and 166) to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 167D and a second electrode 168D, a pacing stimulus 169D, and a channel interface 170D, and the other channel includes a bipolar lead with a first electrode 167E and a second electrode 168E, a pacing stimulus 169E, and a channel interface 170E. Other embodiments may use unipolar leads in which case the neural stimulation pulses are referenced to the can or another electrode. Other embodiments may use tripolar or multipolar leads. In various embodiments, the pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links. Sensor(s) 171 are used by the microprocessor to determine capture (e.g. laryngeal vibrations), the efficacy of therapy (e.g. heart rate, blood pressure) and/or detect events (e.g. cough) or states (e.g. activity sensors).

The figure illustrates a telemetry interface 172 connected to the microprocessor, which can be used to communicate with an external device. The illustrated microprocessor is capable of performing neural stimulation therapy routines and myocardial (CRM) stimulation routines. Examples of NS therapy routines include VST therapies to provide myocardial therapies. NS therapy routines also include routines or algorithms as described in this document. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 19:
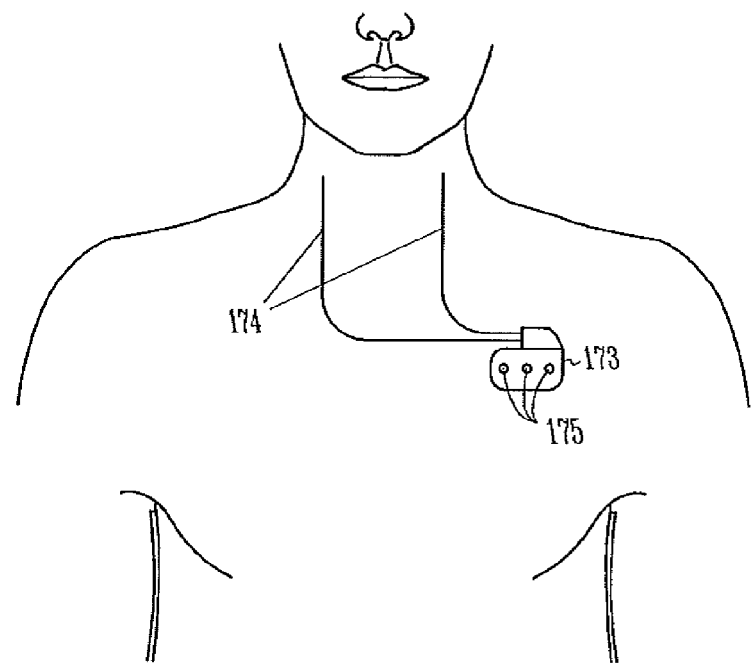
FIG. 19 illustrates a system embodiment in which an IMD is placed subcutaneously or submuscularly in a patient's chest with lead(s) positioned to stimulate a vagus nerve.
Figure 20:
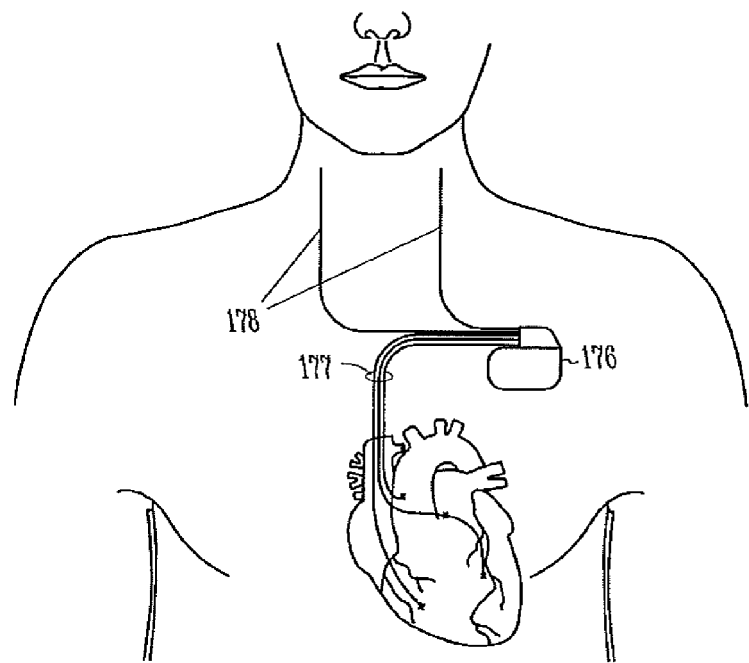
FIG. 20 illustrates an IMD placed subcutaneously or submuscularly in a patient's chest with lead(s) positioned to provide a CRM therapy to a heart, and with lead(s) positioned to stimulate and/or inhibit neural traffic at a neural target, such as a vagus nerve, according to various embodiments.

FIGS. 19-20 illustrate system embodiments adapted to provide VST, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve. FIGS. 19-20 illustrate the use of a lead to stimulate the vagus nerve. Wireless technology could be substituted for the leads, such that a leadless electrode is adapted to stimulate a vagus nerve and is further adapted to wirelessly communicate with an implantable system for use in controlling the VST.

FIG. 19 illustrates a system embodiment in which an IMD 173 is placed subcutaneously or submuscularly in a patient's chest with lead(s) 174 positioned to stimulate a vagus nerve. According to various embodiments, neural stimulation lead(s) 174 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. The illustrated system includes leadless ECG electrodes 175 on the housing of the device. These ECG electrodes are capable of being used to detect heart rate, for example.

FIG. 20 illustrates an IMD 176 placed subcutaneously or submuscularly in a patient's chest with lead(s) 177 positioned to provide a CRM therapy to a heart, and with lead(s) 178 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 21:
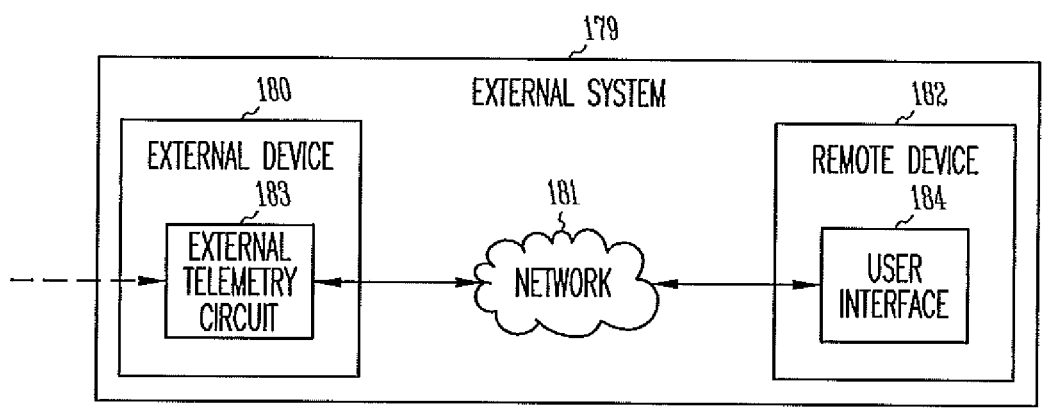
FIG. 21 is a block diagram illustrating an embodiment of an external system.

FIG. 21 is a block diagram illustrating an embodiment of an external system 179. The external system includes a programmer, in some embodiments. In the illustrated embodiment, the external system includes a patient management system. As illustrated, the external system is a patient management system including an external device 180, a telecommunication network 181, and a remote device 182. The external device 180 is placed within the vicinity of an implantable medical device (IMD) and includes an external telemetry system 183 to communicate with the IMD. The remote device(s) is in one or more remote locations and communicates with the external device through the network, thus allowing a physician or other caregiver to monitor and treat a patient from a distant location and/or allowing access to various treatment resources from the one or more remote locations. The illustrated remote device includes a user interface 184. According to various embodiments, the external device includes a neural stimulator, a programmer or other device such as a computer, a personal data assistant or phone. The external device, in various embodiments, includes two devices adapted to communicate with each other over an appropriate communication channel, such as a computer by way of example and not limitation. The external device can be used by the patient or physician to provide feedback indicative of patient discomfort, for example.

As will be understood by one of ordinary skill in the art upon reading and comprehending the present subject matter, various embodiments of the present subject matter improve patient acceptance of therapy, maintain efficacious levels of therapy, allow patient flexibility in therapy management, and generally improve the quality of life of the patient who is receiving the NCT. The modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
 delivering, using a neural stimulator, a vagal stimulation therapy (VST) to a vagus nerve of a patient, wherein delivering the VST includes delivering a therapeutically-effective intensity of neural stimulation to treat a condition, wherein the therapeutically-effective intensity of neural stimulation causes laryngeal vibrations;
 performing a stimulation capture confirmation process multiple times and intermittently during delivery of the VST, wherein performing the stimulation capture confirmation process includes detecting laryngeal vibrations to determine whether the VST is capturing the vagus nerve, wherein detecting laryngeal vibrations includes:
  sensing impedance in a cervical region of a patient to sense changes in impedance characteristics caused by laryngeal vibrations, wherein sensing impedance includes sensing impedance a plurality of times to provide a plurality of sensed impedance values;
  detecting laryngeal vibrations when the VST does not cause cough, including analyzing a plurality of the sensed impedance values to determine whether the VST causes laryngeal vibrations, including whether the VST causes laryngeal vibrations when the VST does not cause cough, and thereby determine whether the VST is capturing the vagus nerve; and
  detecting cough, including analyzing a plurality of the sensed impedance values to determine whether the VST causes cough; and
 maintaining the therapeutically-effective intensity of the neural stimulation for the VST during the stimulation capture confirmation process, including controlling the intensity based on the sensed impedance values to maintain capture of the vagus nerve and avoid cough.

2. The method of claim 1, wherein delivering the VST includes delivering the VST using an electrode in a blood vessel; and sensing impedance includes sensing impedance using the electrode in the blood vessel.

3. The method of claim 2, wherein the blood vessel is an internal jugular vein.

4. The method of claim 1, wherein delivering VST includes delivering a neuro cardio therapy (NCT) to treat a cardiovascular disease, wherein delivering NCT includes delivering NCT as a heart failure therapy or delivering NCT as a hypertension therapy.

5. The method of claim 1, wherein analyzing the plurality of the sensed impedance values includes detecting a change in absolute impedance values, detecting a change in mean of the sensed impedance values, or detecting a change in variability of the sensed impedance values.

6. The method of claim 5, wherein analyzing the plurality of the sensed impedance values includes analyzing the variability of the plurality of the sensed impedance, and analyzing the variability of the plurality of the sensed impedance includes determining a standard deviation or an Inter-Percentile Range of the sensed impedance.

7. A method for detecting laryngeal vibrations and cough and controlling a vagal stimulation therapy (VST) delivered using a neural stimulator to cause laryngeal vibrations and avoid cough, comprising:
 delivering VST, wherein the VST includes a therapeutically-effective intensity of neural stimulation to treat a condition, and the therapeutically-effective intensity of neural stimulation causes laryngeal vibrations; and
 performing a stimulation capture confirmation process multiple times and intermittently during delivery of the VST, wherein the stimulation capture confirmation process includes:
  sensing impedance in a cervical region of a patient to sense changes in impedance characteristics caused by laryngeal vibrations when cough is not present and caused by laryngeal vibrations when cough is present, wherein sensing impedance includes sensing impedance a plurality of times to provide the plurality of sensed impedance values; and
  analyzing a plurality of the sensed impedance values to identify the laryngeal vibrations and identify the cough, wherein sensing impedance includes:
   sensing impedance changes in or near a carotid sheath; or sensing impedance using a lead in an internal jugular vein; and controlling an intensity of the VST delivered using the neural stimulator based on the sensed impedance to maintain the therapeutically-effective intensity of the neural stimulation for VST during the stimulation capture confirmation process that causes laryngeal vibrations and avoids cough.

\* \* \* \* \*